United States Patent [19]

Wenander

[11] 4,188,945
[45] Feb. 19, 1980

[54] SURGICAL CLOTH

[75] Inventor: Björn Wenander, Nötegång, Sweden

[73] Assignee: Triplus Sjukvårdsprodukter AB, Sweden

[21] Appl. No.: 933,587

[22] Filed: Aug. 14, 1978

[30] Foreign Application Priority Data

Aug. 26, 1977 [SE] Sweden .............................. 7709587

[51] Int. Cl.² ............................................. A61B 19/06
[52] U.S. Cl. ................................................. 128/132 D
[58] Field of Search ................... 128/132 D, 283, 292, 128/294, 295; 2/50, 174, 172, 87-89

[56] References Cited

U.S. PATENT DOCUMENTS

| 1,503,117 | 7/1924 | Crawford et al. | 2/50 |
| 2,093,483 | 9/1937 | Sackett | 2/50 |
| 2,803,013 | 8/1957 | Freiberger | 2/50 |
| 3,435,821 | 4/1969 | Bennett | 128/132 D |
| 3,540,433 | 11/1970 | Brockman | 128/283 |

*Primary Examiner*—Lawrence W. Trapp
*Attorney, Agent, or Firm*—Holman & Stern

[57] ABSTRACT

A surgical cloth intended as a protection of the wound edges of an incision. The surgical cloth is provided with a central hole, which uncovers the operation area. A hem surrounds the hole and a rigid but flexible thread is introduced into the hem through an opening. The thread has a loop at one end and the opposite end of the thread is passed through said loop. The size of the hole can be adjusted by tightening or loosening the thread.

1 Claim, 4 Drawing Figures

SURGICAL CLOTH

BACKGROUND OF THE INVENTION

The present invention refers to a surgical cloth provided with a central hole, which uncovers the operation area, said cloth being intended as a protection of the wound edges around an incision.

Previously known surgical cloths of this kind are usually provided with a plastic ring around the hole, which is introduced into the wound cavity, so that the surgical cloth surrounds as well the wound edges as the surrounding operation area. This kind of operation cloth can be used only for incisions with a length corresponding to the diameter of the plastic ring and it is therefore necessary to have surgical cloths with plastic rings of different sizes. It is not unusual that the operation area has to be enlarged during the operation, which means that a new surgical cloth with a larger plastic ring has to be used. These circumstances have involved that surgical cloths of this known type have been used only to a very limited extent and since the protection of the wound edges against repeated contamination during the operation is an important demand, it has hitherto been a clearly expressed desire to provide a surgical cloth, which easily can be adjusted to a desired size but still also is simple to introduce into the wound cavity and which without a previous time-requiring handling is ready for immediate introduction into the wound. Since the surgical cloth is a throw-away article it must also be simple and cheap to manufacture and adapted for sterilization.

SUMMARY OF THE INVENTION

The purpose of the present invention is to provide a surgical cloth which fulfils all these demands, which has been achieved by a cloth being provided with a hem surrounding the hole, the hem being provided with an opening through which a rigid, flexible thread is intended to be introduced, one of the ends of the thread is provided with a loop through which the opposite end of the thread is passed, said thread having a length exceeding that of the hem surrounding the hole and the thread being displaceable in the hem for adjusting the size of the hole.

BRIEF DESCRIPTION OF THE DRAWINGS

The invention will now be further described with reference to the accompanying drawing, which shows an embodiment.

DESCRIPTION OF A PREFERRED EMBODIMENT

Figure 1:
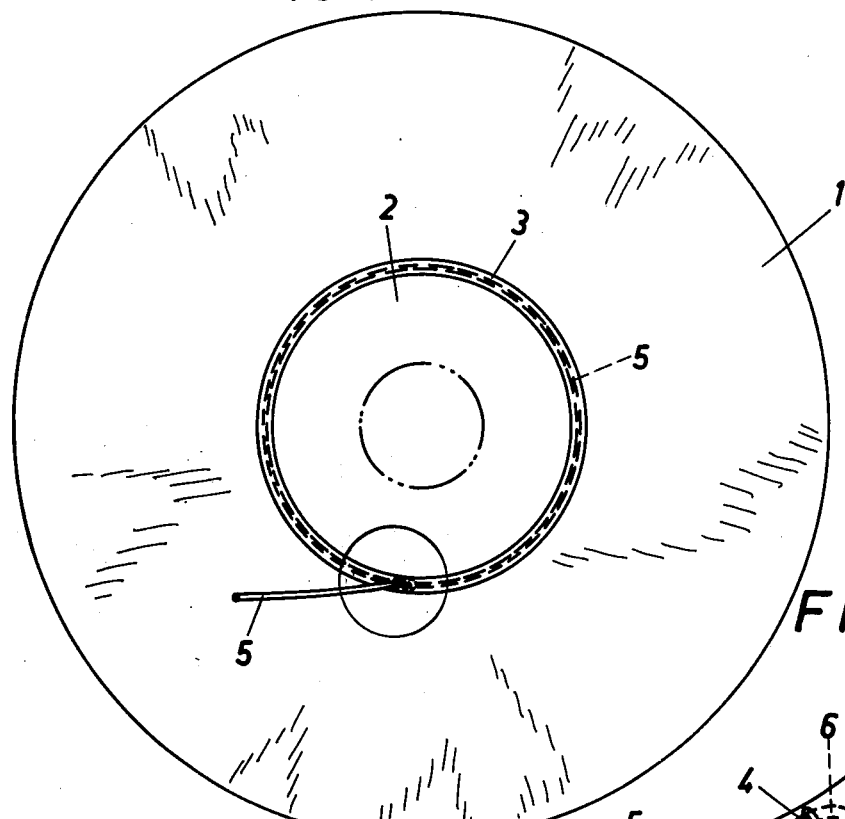
FIG. 1 shows from above the surgical cloth according to the invention.
Figure 2:
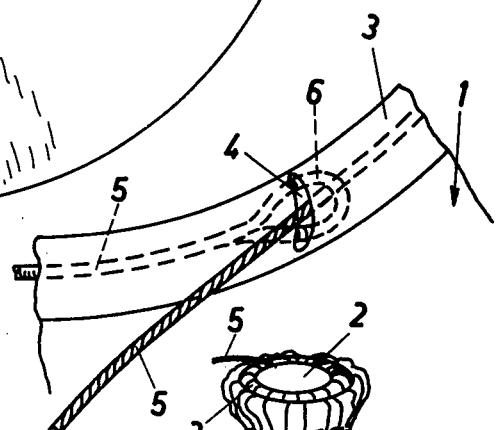
FIG. 2 shows on a larger scale the encircled portion of FIG. 1.

The surgical cloth 1 according to the embodiment is substantially circular and has a central hole 2. Around the hole 2 a circumferential hem 3 is arranged, which is provided with an opening 4, through which a rigid, substantially straight but flexible thread 5 of a plastic material is introduced. The thread is at one of its ends provided with a loop 6 located just opposite the opening 4 and the opposite end of the thread is passed through said loop. The thread 5 has a large free space in the hem 3 and by tightening the thread the free opening of the hole 2 is adjusted to a desired size. Since the thread is rigid but also flexible it will always keep the hole stretched to the chosen size, which is important since the application of the surgical cloth in the wound cavity thereby is considerably facilitated as well as the adjustment of the hole to a desired size.

The loop 6 can possibly be so designed, that the thread end which is passed through the loop is exerted to a frictional drag, at which it is secured that the chosen size of the hole is maintained.

Figure 4:
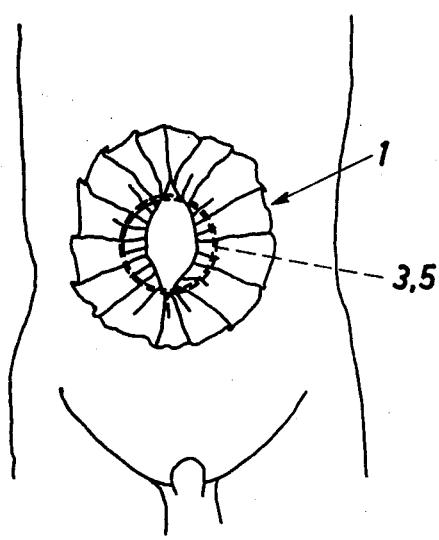
FIG. 4 shows the surgical cloth applied at a stomach operation.
Figure 3:
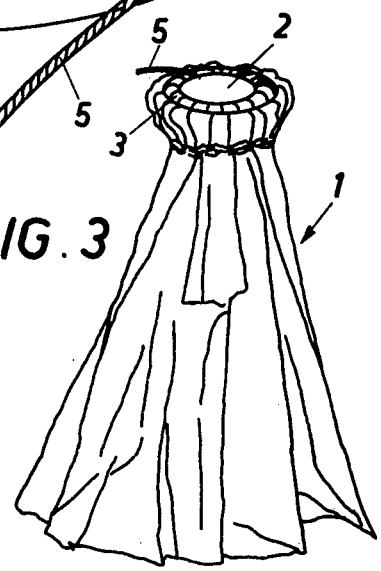
FIG. 3 is a perspective view of the surgical cloth with a contracted central hole for introduction into a wound cavity.

The surgical cloth is used in the following way. After the cloth has been removed from the sterile package in which it is delivered, the cloth is brought together around the contracted central hole 2 as is shown in FIG. 3. The portion around the contracted central hole 2 is after that introduced into the wound cavity (incision), so that the ring-shaped thread 5 in the hem 3 of the surgical cloth will be located under the wound edges of the skin, and the central hole 2 is enlarged to a desired size, as is shown in FIG. 4. The surgical cloth is after that placed over the skin area surrounding the incision, so that the wound edges are effectively protected from repeated contact and contamination at the same time as the wound edges are visualized.

I claim:

1. A surgical cloth provided with a central hole, which uncovers the operation area, said cloth being intended as a protection of the wound edges around an incision, wherein the cloth is provided with a hem surrounding the hole, the hem being provided with an opening through which a rigid, flexible thread is intended to be introduced, one of the ends of the thread being provided with a loop through which the opposite end of the thread is passed, said thread having a length exceeding that of the hem surrounding the hole and the thread being displaceable in the hem for adjusting the size of the hole.

* * * * *